United States Patent [19]

VandenBerg

[11] Patent Number: Plant 6,774

[45] Date of Patent: May 2, 1989

[54] CHRYSANTHEMUM PLANT NAMED INDIO

[75] Inventor: Cornelis P. VandenBerg, Salinas, Calif.

[73] Assignee: Yoder Brothers, Inc., Barberton, Ohio

[21] Appl. No.: 135,299

[22] Filed: Dec. 21, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Indio particularly characterized by its flat capitulum form; anemone capitulum type; yellow ray floret color with a yellow anemone cushion; diameter across face of capitulum of up to 7 cm at maturity when grown as a pinched spray pot mum, with diameter of anemone cushion of up to 2.5 cm; uniform eight week photoperiodic flowering response to short days; short plant height when grown as a pinched pot mum; and spreading and prolific branching pattern.

3 Drawing Sheets

The present invention comprises a new and distinct cultivar of Chrysanthemum, botanically known as *Chrysanthemum morifolium,* Ramat., and referred to by the cultivar name Indio.

Indio, identified as 83517007, was originated from a cross made by Cornelis P. VandenBerg in a controlled breeding program in Salinas, Calif. in 1983.

The female parent of Indio was the cultivar identified as Pert, disclosed in U.S. Plant Pat. No. 4,764. The male parent of Indio was an unnamed seedling, identified as 80100001.

Indio was discovered and selected as one flowering plant within the progeny of the stated cross by Cornelis P. VandenBerg in September of 1983, in a controlled environment in Salinas, Calif.

The first act of asexual reproduction of Indio was accomplished when vegetable cuttings were taken from the initial selection in December of 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Indio are firmly fixed and are retained through successive generations of asexual reproduction.

Indio has not been observed under all possible environmental conditions. The phenotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits having been repeatedly observed and are determined to be basic characteristics of Indio, which, in combination, distinguish this Chrysanthemum as a new and distinct cultivar:

1. Flat capitulum form.
2. Anemone capitulum type.
3. Yellow ray floret color, with a yellow anemone cushion.

4. Diameter across face of capitulum of up to 7 cm at maturity, with a diameter of anemone cushion of up to 2.5 cm when grown as a pinched spray pot mum.
5. Uniform eight week photoperiodic flowering response to short days.
6. Short plant height requiring 7 to 14 long days after pinch prior to short days and 1 application of 2500 ppm B-9 SP to attain a flowered plant height of 25 to 35 cm for year-round flowerings when grown as a pinched pot mum.
7. Branching pattern is spreading and prolific.

The accompanying photographic drawings show typical inflorescence and leaf characteristics of Indio, with the colors being as nearly true as possible with illustrations of this type.

Sheet 1 is a color photograph of Indio grown as a pinched spray pot mum.

Sheet 2 is a black and white photograph of three views of the inflorescence of Indio.

Sheet 3 is a black and white photograph showing the upper and under sides of the leaves of Indio at three stages of development (mature, intermediate and immature).

Of the commercial cultivars known to the inventor, the most similar in comparison to Indio is the female parent Pert. Reference is made to attached Chart A, which compares certain characteristics of Indio to the same characteristics of Pert.

Similar traits are capitulum form, plant height and flowering response. Ray floret color of Indio is a lighter yellow than the color of Pert. Indio has an anemone capitulum type, whereas Pert has a daisy capitulum type. Indio has a more prolific branching pattern and slightly smaller diameter of capitulum than Pert.

In the following description, color references are made to The Royal Horticultural Society Colour Chart. The color values were determined on plant material grown as a pinched spray pot mum in Salinas, Calif. on June 11, 1987.

Classification:

*Botanical.*—*Chrysanthemum morifolium,* Ramat., cv. Indio.

*Commercial.*—Anemone spray pot mum.

INFLORESCENCE

A. Capitulum:

*Form.*—Flat.

*Type.*—Anemone.

*Diameter across face.*—Up to 7 cm at maturity.

*Diameter of anemone cushion.*—Up to 2.5 cm.

B. Corolla of ray florets:

*Color (general tonality from a distance of three meters).*—Yellow.

*Color (upper surface).*—5A.

*Color (under surface).*—6B to 6C.

*Shape.*—Flat, oblong.

C. Corolla of disc florets (Anemone Cushion):

*Color (mature).*—Closest to 13B.

*Color (immature).*—Closest to 154A.

D. Reproductive organs:

*Androecium.*—Present on disc florets only; moderate pollen.

*Gynoecium.*—Present on both ray and disc florets.

PLANT

A. General appearance:

*Height.*—Short; 25 to 35 cm as a pinched spray pot mum with 7 to 14 long days after pinch prior to short days and 1 application of 2500 ppm B-9 SP.

*Branching pattern.*—Spreading and prolific.

B. Foliage:

*Color (upper surface).*—137A to 147A.

*Color (under surface).*—147B.

*Shape.*—Lobed and serrated.

CHART A

Comparison of Indio and Pert

| Cultivar | Ray Floret Color | Capitulum Form and Type | Branching Pattern |
|---|---|---|---|
| Indio | Yellow | Flat Anemone | Spreading and prolific |
| Pert | Dark yellow | Flat Daisy | Semi-spreading |

| Cultivar | Diameter across face of capitulum | Plant height | Flowering response period |
|---|---|---|---|
| Indio | Up to 7 cm | Short | 8 weeks |
| Pert | 70–90 mm | Short | 8 weeks |

Comparisons made of plants grown as pinched pot mums in Salinas, California

I claim:

1. A new and distinct cultivar of Chrysanthemum plant named Indio, as illustrated and described, and parts thereof.

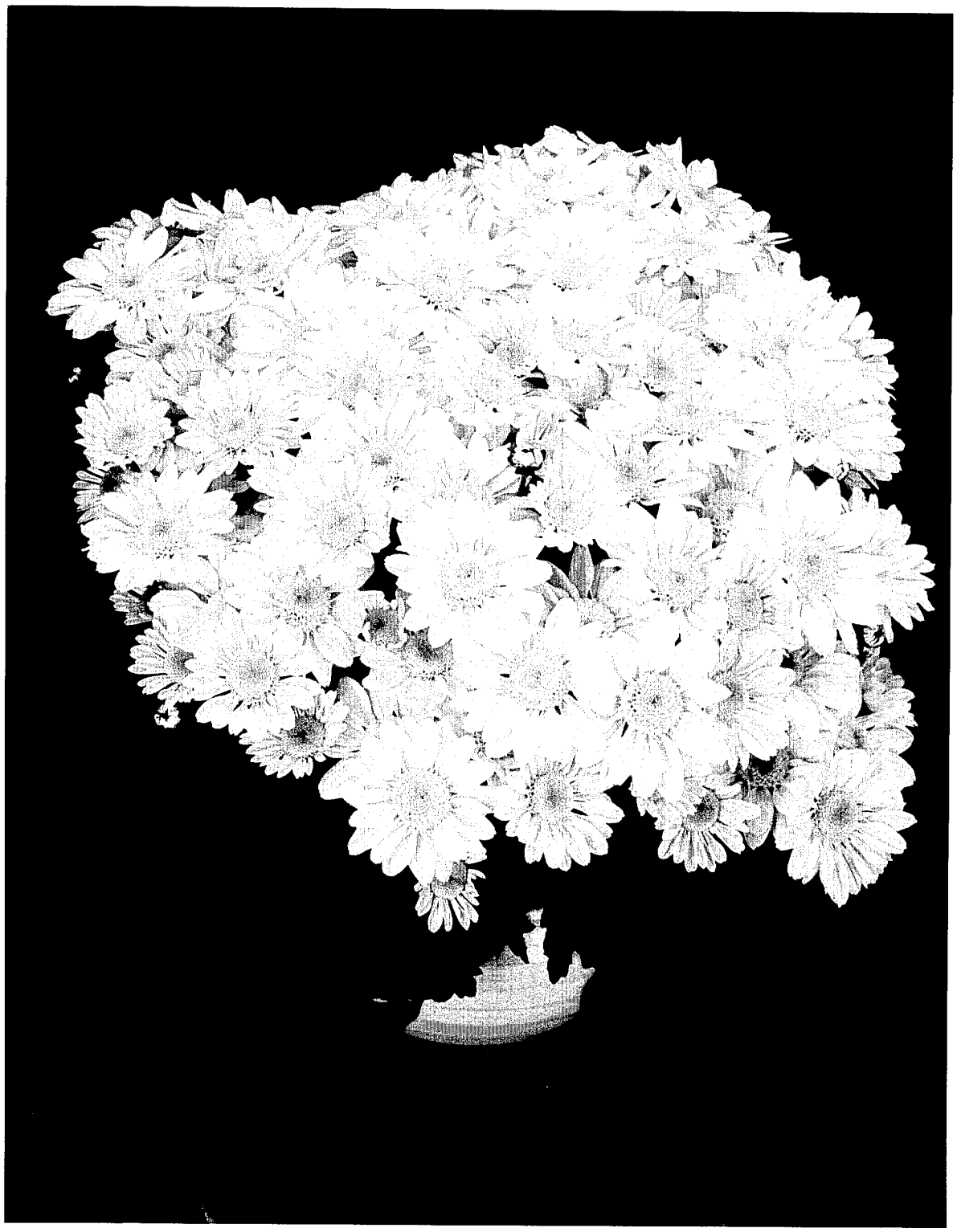

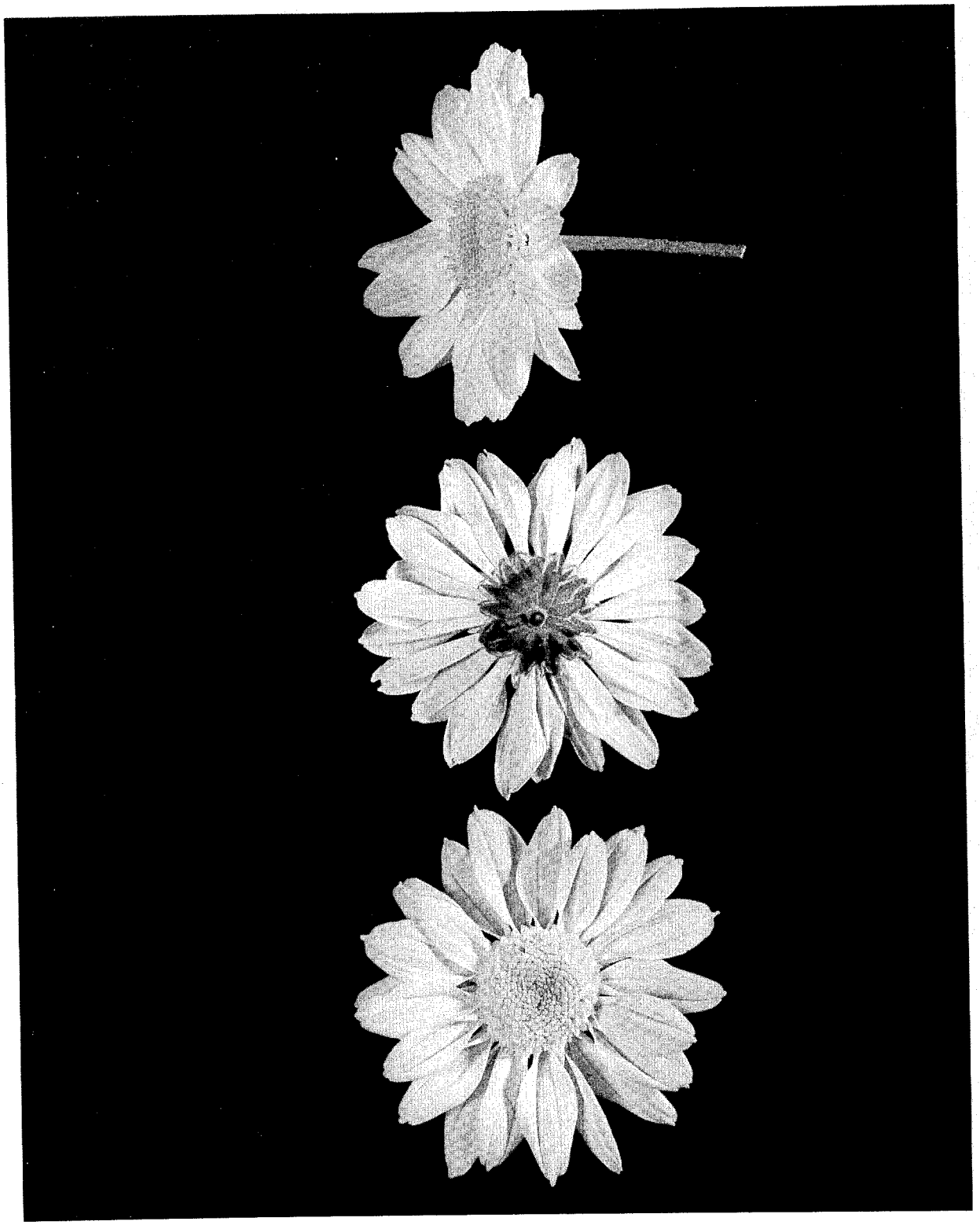

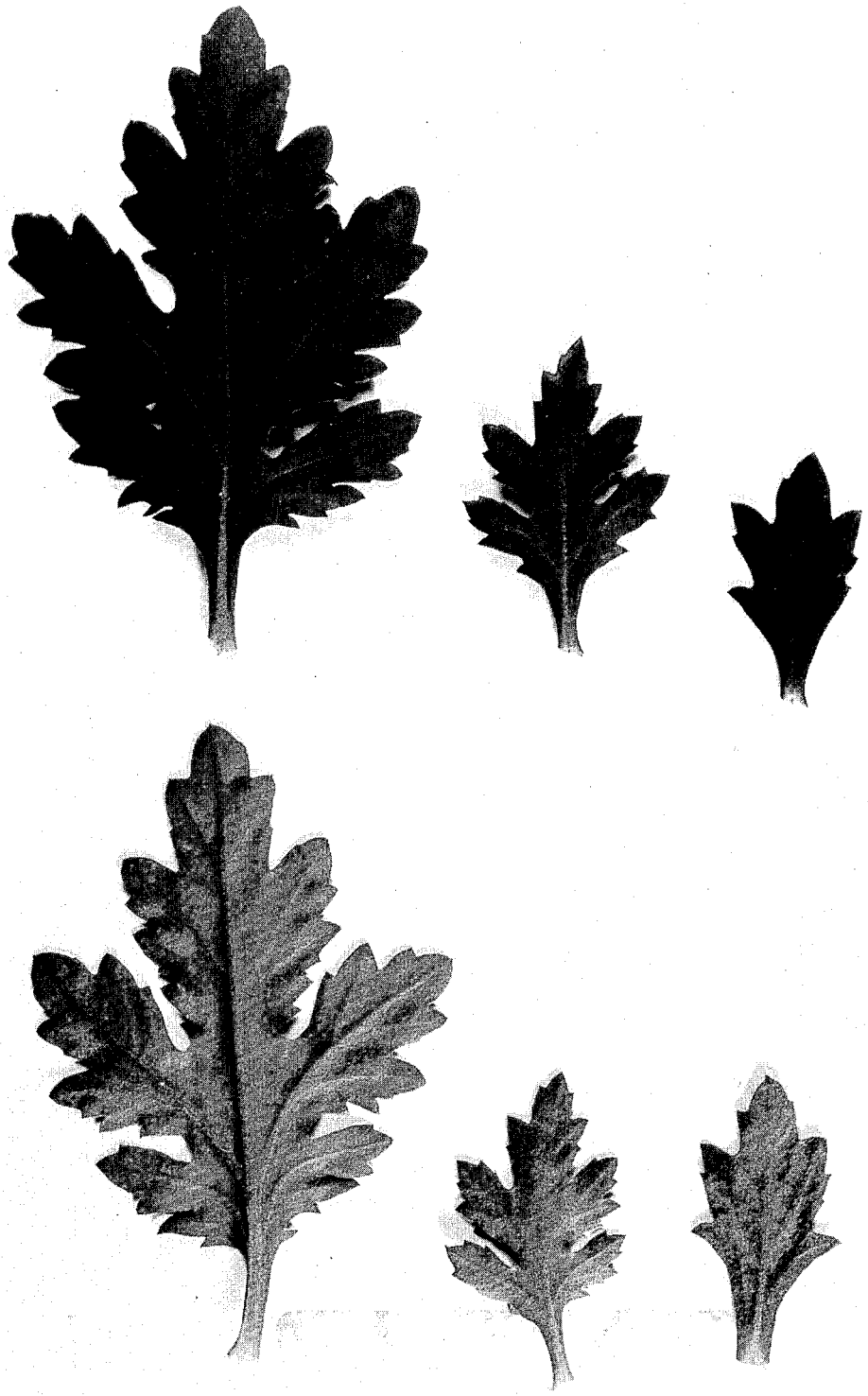

* * * * *